United States Patent
Miyasa et al.

(10) Patent No.: US 8,908,946 B2
(45) Date of Patent: *Dec. 9, 2014

(54) INFORMATION PROCESSING APPARATUS AND ITS CONTROL METHOD AND DATA PROCESSING SYSTEM

(71) Applicant: Canon Kabushiki Kaisha, Tokyo (JP)

(72) Inventors: Kazuhiro Miyasa, Yokohama (JP); Hiroshi Imamura, Tokyo (JP); Masaaki Imaizumi, Tokyo (JP); Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/673,770

(22) Filed: Nov. 9, 2012

(65) Prior Publication Data

US 2013/0070987 A1 Mar. 21, 2013

Related U.S. Application Data

(63) Continuation of application No. 13/070,143, filed on Mar. 23, 2011, now Pat. No. 8,331,640, which is a continuation of application No. 12/562,204, filed on Sep. 18, 2009, now Pat. No. 7,933,437.

(30) Foreign Application Priority Data

Sep. 25, 2008 (JP) ................................ 2008-246596

(51) Int. Cl.
*G06K 9/00* (2006.01)
*G06T 7/00* (2006.01)
*G06F 19/00* (2011.01)
*G06K 9/32* (2006.01)
*G06F 17/00* (2006.01)

(52) U.S. Cl.
CPC ............ *G06T 7/0012* (2013.01); *G06F 19/321* (2013.01); *G06K 9/3233* (2013.01); *G06K 2209/05* (2013.01)
USPC .......................................... 382/128; 707/802

(58) Field of Classification Search
CPC ............ G06K 9/00; G06T 7/00; G06F 19/321
USPC .............. 382/128–134; 378/4, 8, 21–27, 901; 600/407, 410, 411, 425, 427; 128/920, 128/922; 707/605, 760, 769, 806, 809, 802, 707/803

See application file for complete search history.

(56) References Cited

U.S. PATENT DOCUMENTS 5,086,392 A * 2/1992 Nakajima ...................... 382/128
6,108,635 A * 8/2000 Herren et al. ...................... 705/2

(Continued)

FOREIGN PATENT DOCUMENTS

JP 1-107739 4/1989
JP 8-263625 10/1996

(Continued)

OTHER PUBLICATIONS

D.G. Lowe, "Object Recognition from Local Scale-Invariant Features", *Proc. of IEEE Conf. on Computer Vision* (ICCV), pp. 1150-1157 (1999).

(Continued)

*Primary Examiner* — Abolfazl Tabatabai
(74) *Attorney, Agent, or Firm* — Fitzpatrick, Cella, Harper & Scinto

(57) ABSTRACT

In order to provide a technology which allows efficient understanding of images of a disease locus and diagnosis supporting information for the images, an information processing apparatus comprises: an input unit which inputs object identification information for identifying an object; an acquiring unit which acquires one or more schemas related to the object and medical image data related to the schema, an identification unit which identifies a disease locus region in medical image data respectively related to each of the one or more schemas, a time-series schema generating unit which generates a time-series schema of the disease locus, a time-series image data generating unit which generates time-series image data of the disease locus, and a display output unit which synchronizes and outputs the time-series schema of the disease locus and the time-series image data of the disease locus.

14 Claims, 10 Drawing Sheets

(56) References Cited

U.S. PATENT DOCUMENTS

| | | | |
|---|---|---|---|
| 2008/0039707 A1 | 2/2008 | Sugiyama et al. | 600/407 |
| 2010/0074488 A1 | 3/2010 | Ishikawa et al. | 382/128 |
| 2010/0231605 A1 | 9/2010 | Yoshiyuki et al. | 345/619 |

FOREIGN PATENT DOCUMENTS

| | | |
|---|---|---|
| JP | 2000-222503 | 8/2000 |
| JP | 2004-033539 | 2/2004 |
| JP | 2006-181146 | 7/2006 |
| JP | 2007-325742 | 12/2007 |
| JP | 2008-043524 | 2/2008 |

OTHER PUBLICATIONS

M. Kass et al., "Sankes: Active Contour Models", *Int'l Journal of Computer Vision* (4), pp. 321-331 (1988).

Y. Ke et al., "PCA-Shift: A More Distinctive Representation for Local Image Descriptors", *Proc. of IEEE Conf. on Computer Vision and Pattern Recognition* (CVPR), pp. 511-517 (2004).

\* cited by examiner

F I G. 3
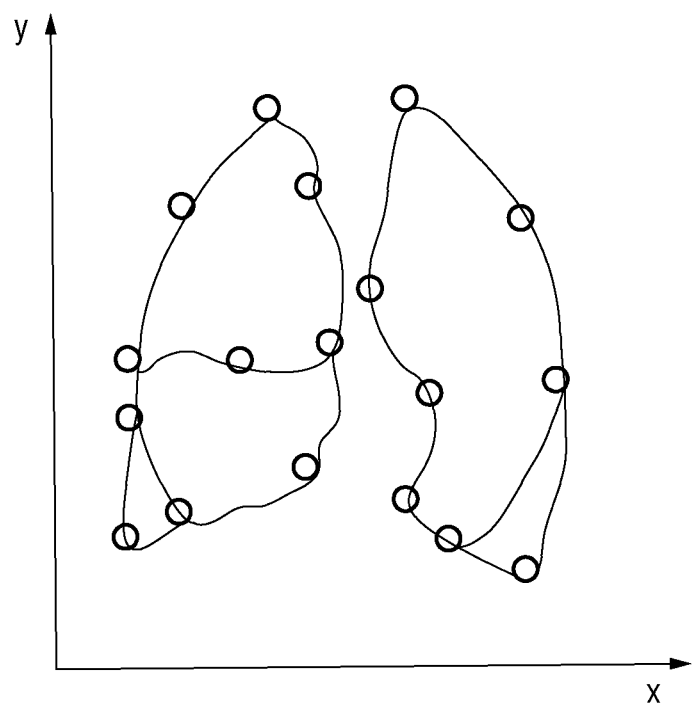

F I G. 10

| DATE OF IMAGE CAPTURING | EXAMINATION DATA NUMBER | COORDINATE OF NODE CENTER | EFFECTIVE RADIUS OF NODE(mm) |
|---|---|---|---|
| 20XX/01/10 | 1 | (155, 210, 247) | 7 |
| 20XX/02/10 | 2 | (158, 212, 250) | 13 |
| 20XX/03/10 | 3 | (156, 214, 246) | 15 |
| 20XX/04/10 | 4 | (156, 211, 249) | 22 |
| 20XX/05/10 | 5 | (157, 212, 247) | 21 |
| 20XX/06/10 | 6 | (156, 211, 248) | 20 |

INFORMATION PROCESSING APPARATUS AND ITS CONTROL METHOD AND DATA PROCESSING SYSTEM

RELATED APPLICATIONS

This is a continuation of application Ser. No. 13/070,143, filed Mar. 23, 2011, which is a continuation of application Ser. No. 12/562,204, filed Sep. 18, 2009 and claims benefit of those applications under 35U.S.C. §120, and claims benefit under 35U.S.C. §119 of Japanese patent application no. 2008-246596, filed Sep. 25, 2008. The entire contents of each of the mentioned prior applications are incorporated herein by reference.

BACKGROUND OF THE INVENTION

1. Field of the Invention

The present invention relates to an information processing apparatus which supports creating medical reports (carte), image diagnosis reports, etc. In particular, the present invention relates to a technique of displaying schema drawn by doctors on medical documents.

2. Description of the Related Art

In the field of medical care, devices for generating medical pictures for examination of the interior of patients' bodies include Computed Radiography (CR) devices, Computed Tomography (CT) devices, Magnetic Resonance Imaging (MRI) devices, and Ultrasound System devices. Physicians display medical images taken by these devices on a monitor, from which conditions and temporal changes of troubled areas are observed, and results of an image diagnosis are recorded in an image diagnostic report as findings information. Doctors, when making diagnostic confirmations for the troubles, record conditions of patients and disease names in their respective medical reports. It is possible to attach schema illustrating features of diagnosis for the troubled areas to allow easy visual recognition of the diagnosis made by the doctor concerning the troubled areas.

Traditionally, schema were recorded on paper medical documents by freehand drawing. However, with the spread of medical information systems such as Hospital Information System (HIS) and Picture Archiving and Communication Systems (PACS) in recent years, advancement of medical document computerization including electronic carte has taken place, which is also followed by gradual computerization of schema.

When creating a schema as electronic data, it is possible to input figures having arbitrary shapes into a computer as line-drawing information using an input device such as a mouse or a tablet. However, when creating an illustration (called "basic schema") indicating body structures in a schema, it is necessary to draw complicated shapes, which cannot be easily drawn using a mouse or a tablet.

To address this, Japanese Patent Laid-Open No. 2006-181146 (patent reference 1) discloses a technique of storing a plurality of basic schema templates, from which a desired basic schema can be selected by the physician. According to this method, it is possible to create a schema by selecting a basic schema and drawing simple figures and explanatory paragraphs regarding conditions of the troubled part (disease locus) on the schema (called "disease locus schema"). Further, Japanese Patent Laid-Open 2000-222503 (patent reference 2) suggests a device that not only stores basic schema, but also stores figures and explanatory paragraphs that comprise schema of disease loci and arrows connecting them as separate electronic data. From this, it is possible to easily perform manipulation of existing schema, such as changing, moving or deleting the included texts and figures.

Furthermore, D. G. Lowe, "Object recognition from local scale-invariant features", Proc. of IEEE International Conference on Computer Vision (ICCV), pp. 1150-1157, 1999 (non-patent reference 1), and Y. Ke, R. Sukthankar, "PCA-SHIFT: A more distinctive representation for local image descriptors", Proc. of IEEE Conference on Computer Vision and Pattern Recognition(CVPR), pp. 511-517, 2004 (non-patent reference 2) respectively disclose SHIFT feature amount and PCA-SHIFT feature amount. For example, in a basic schema, it is possible to use calculated feature amounts as structural information of body parts drawn in the basic schema. Further, Kass M, Witkin A, Terzopoulos D: Snakes:active contour models. International Journal of Computer Vision 1 (4):321-331, 1988 (non-patent reference 3) suggests an area division method by a variable shape model. For example, by applying the variable shape model on an image or a schema, it is possible to extract areas of disease loci surrounded by edges.

In clinical settings, diagnoses aiming to make long term observations such as progression of disease loci like tumors and healing processes, are performed. For such long term observations, it is possible to refer to past diagnostic information regarding disease loci in which the mental picture of the physician is coupled to explanatory paragraphs, by using not only images that were captured before, but also checking schema created in the past.

Previously, as indicated in Japanese Patent Laid-Open Nos. 1-107739 (patent reference 3) and 8-263625 (patent reference 4), physicians determined temporal changes of disease loci, by displaying on an image display unit such as a CRT display device a plurality of images captured at different time points of the same subject (to be referred to as an examined patient). In such cases, images taken at different time points are simultaneously displayed or alternated, and viewers such as physicians made comparative observations of the plurality of images being displayed, determining temporal changes of troubled parts.

However, with the above-mentioned method, although it is possible to understand temporal changes in disease loci from the captured images of the disease loci, it is not possible to understand diagnostic information (schema) showing how the physician characterized the disease loci and arrived at the decision. For this reason, physicians had to separately refer to captured images and the information pertaining to the images.

SUMMARY OF THE INVENTION

According to one aspect of the present invention, an information processing apparatus which acquires a schema of an object and corresponding medical image data of the schema from an examination record database and displays them on a display unit, the schema records at least time information and disease locus information, wherein the information processing apparatus comprises: an input unit which inputs object identification information for identifying an object; an acquiring unit which acquires, from the examination record database based on the object identification information inputted by the input unit, one or more schemas related to the object and medical image data related to the schema; an identification unit which identifies a disease locus region in medical image data respectively related to each of the one or more schemas, based on the disease locus information recorded in each of the one or more schemas; a time-series schema generating unit which generates a time-series schema of the disease locus based on respective time information of each of the one or more schemas and respective disease locus information recorded in each of the one or more schemas; a time-series image data generating unit which generates time-series image data of the disease locus based on respective time information of each of the one or more schemas and respective disease locus images in medical image data related to each of the one or more schemas; and a display output unit which synchronizes and outputs the time-series schema of the disease locus and the time-series image data of the disease locus to the display unit for display.

According to another aspect of the present invention, an information processing apparatus which acquires a schema of an object and corresponding medical image data of the schema from an examination record database and displays them on a display unit, the schema records at least time information and disease locus information, wherein the information processing apparatus comprises: an input unit which inputs object identification information for identifying an object; an acquiring unit which acquires, from the examination record database based on the object identification information inputted by the input unit, one or more schemas related to the object and medical image data related to the schema; an identification unit which identifies a disease locus region in medical image data respectively related to each of the one or more schemas, based on the disease locus information recorded in each of the one or more schemas; a deriving unit which derives an image feature amount of the identified disease locus area for each of the medical image data respectively related to each of the one or more schemas; a time-series schema generating unit which generates a time-series schema of the disease locus based on respective time information of each of the one or more schemas and respective disease locus information recorded in each of the one or more schemas; a time-series image feature amount data generating unit which generates time-series data of image feature amounts of the disease locus based on time information of each of the one or more schemas and on image feature amounts of disease locus area of medical image data related to each of the one or more schemas; and a display output unit which synchronizes and outputs the time-series schema of the diseased locus and the time-series data of image feature amounts of the disease locus to the display unit for display.

According to still another aspect of the present invention, a method of controlling an information processing apparatus which acquires a schema of an object and corresponding medical image data of the schema from an examination record database and displays them on a display unit, the control method comprises: a step of inputting object identification information for identifying the object; a step of acquiring, from the examination record database based on the object identification information, one or more schemas related to the object and medical image data related to the schema; a step of identifying a disease locus region in medical image data respectively related to each of the one or more schemas, based on the disease locus information recorded in each of the one or more schemas; a step of generating a time-series schema of the disease locus based on respective time information of each of the one or more schemas and respective disease locus information recorded on each of the one or more schemas; a step of generating time-series image data of the disease locus based on the respective time information of each of the one or more schemas and respective disease locus images in medical image data related to each of the one or more schemas; and a step of outputting the time-series schema of the diseased locus and the time-series image data of the diseased locus, which are synchronized, to the display unit.

According to yet another aspect of the present invention, a data processing system comprises an examination data record database which records schema of objects and corresponding medical image data of the schema, and an information processing apparatus which accesses the examination record database, acquires the schema of an object and corresponding medical image data and displays them on a display unit, wherein the information processing apparatus comprises: an input unit which inputs object identification information for identifying the object; an acquiring unit which acquires, from the examination record database based on the object identification information inputted by the input unit, one or more schemas related to the object and medical image data related to the schema; an identification unit which identifies a disease locus region in medical image data respectively related to each of the one or more schemas, based on the disease locus information recorded in each of the one or more schemas; a time-series schema generating unit which generates a time-series schema of the disease locus based on respective time information of each of the one or more schemas and respective disease locus information recorded on each of the one or more schemas; a time-series image data generating unit which generates time-series image data of the disease locus based on the respective time information of each of the one or more schemas and respective disease locus images in medical image data related to each of the one or more schemas; and a display output unit which synchronizes and outputs the time-series schema of the diseased locus and the time-series image data of the diseased locus to the display unit for display.

According to the present invention, it is possible to provide a technique which enables efficient understanding of captured images of troubled parts and supporting diagnostic information of the images.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 3 shows characteristic features of a basic schema.

FIG. 10 is a table of temporal changes of a disease locus.

DESCRIPTION OF THE EMBODIMENTS

Preferred embodiments of the present invention will be explained below with reference to figures. Embodiments provided below are only examples, and are not intended to restrict scope of the present invention.

(First Embodiment)

An example of a diagnosis supporting apparatus in a data processing system will be explained below as a first embodiment of the present invention.

<Apparatus Composition>

Figure 1:
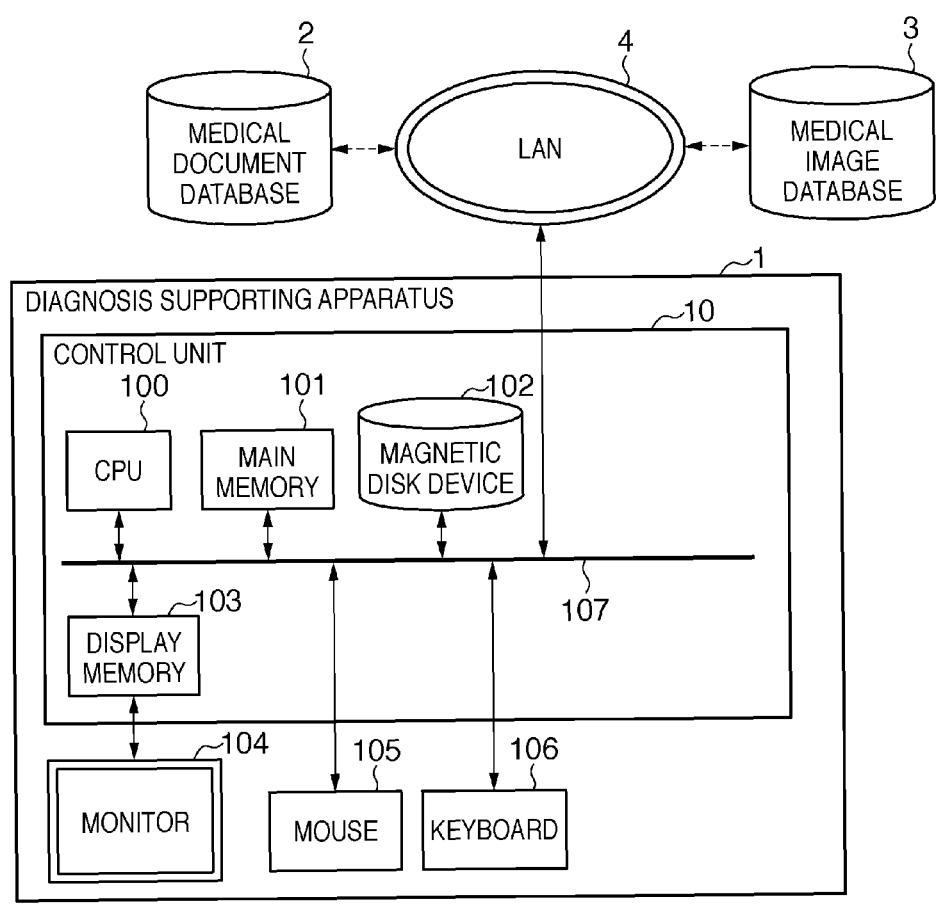
FIG. 1 indicates configuration of a diagnosis supporting apparatus 1 according to a first embodiment of the present invention.

FIG. 1 indicates configuration of a diagnosis supporting apparatus 1 according to the first embodiment of the present invention.

The diagnosis supporting apparatus 1 has a control unit 10, a monitor (display unit) 104, a mouse 105, and a keyboard 106. The control unit 10 has a central processing unit (CPU) 100, a main memory 101, a magnetic disc 102, and a display memory 103. Various types of control, such as communication between a medical document database 2 and a medical image database 3, overall control of the diagnosis supporting apparatus 1, etc, are performed by execution of programs stored in the main memory 101 by the CPU.

Further, the diagnosis supporting apparatus 1 is connected to the medical image database 3 which can capture image of examination subjects. The medical image database 3 stores image data captured at medical image capturing devices such as an X-ray CT device, an MRI device, a US device, an X-ray device, or a nuclear medical device. The medical document database 2 (examination record database) stores document data such as electronic carte, image diagnosis reports, previously composed schema, etc.

The CPU 100 primarily controls each of the structural components of the diagnosis supporting apparatus 1. The main memory 101 serves roles such as storing control programs executed by the CPU 100, and providing work area when programs are executed by the CPU 100. The magnetic disc 102 stores an operating system (OS), device drives of peripheral devices, application software of various types including programs for performing diagnosis support processing, etc. The display memory 103 temporarily stores data to be displayed on the monitor 104. The monitor 104 is, for example a CRT monitor or an LCD monitor, and displays images based on the data from the display memory 103. The mouse 105 and the keyboard 106 respectively execute pointing input and text input performed by the user. Above-mentioned structural components are communicably connected to each other by a common BUS 107.

In the first embodiment, the diagnosis supporting apparatus 1 can read out medical document data and medical image data, such as electronic carte, by accessing the medical document database 2 and the medical image database 3 via LAN 4. Also, it is possible to connect storage devices, such as an FDD, a CD-RW drive, an MO drive, a ZIP drive, etc, to the diagnosis supporting apparatus 1 and read out medical images and such from these storage devices. Further, it is also possible to acquire medical images and such directly from medical image capturing devices via the LAN 4.

<Apparatus Operation>

Figure 2:
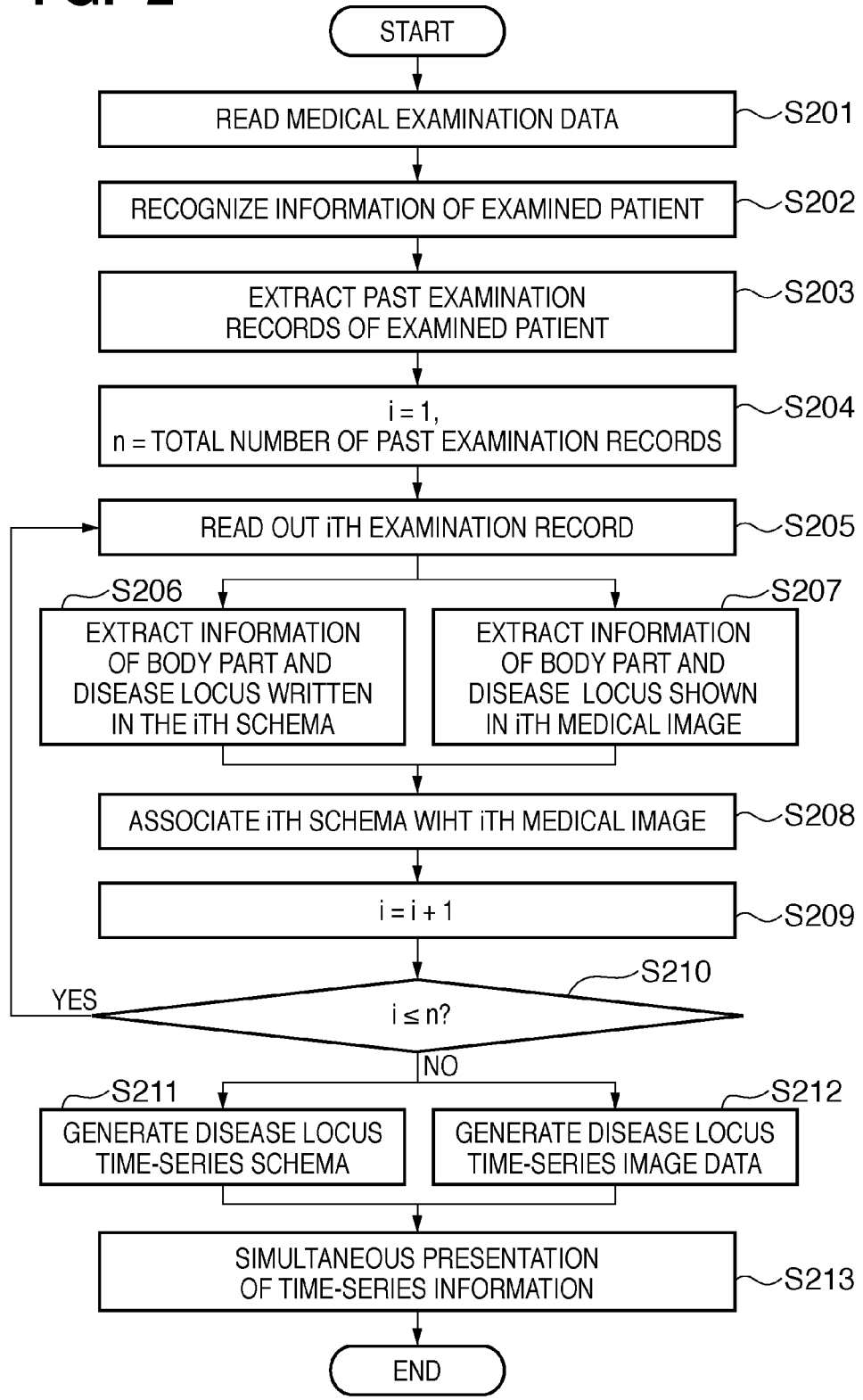
FIG. 2 is a processing flowchart of the diagnosis supporting apparatus 1 according to the first embodiment.

FIG. 2 is an operation flowchart of the diagnosis supporting apparatus 1 of the first embodiment. The processing shown in FIG. 2 is realized by having the CPU 100 perform the program stored in the main memory 101.

At step S201, the CPU 100 performs processing to input medical examination data (medical images and electronic carte) intended for diagnostic imaging, in response to input by the mouse 105 or the keyboard 106. This input processing of medical examination data is, for example as mentioned above, processing in which the CPU 100 receives medical images or medical carte from the medical document database 2 and the medical image database 3 via the LAN 4. Further, as mentioned above, it can also be arranged to have the CPU 100 read out equivalent data from a storage device connected to the diagnosis supporting apparatus 1, for example an FDD, a CD-RW drive, an MO drive, a ZIP drive, etc.

At step S202, the CPU 100 performs processing to recognize information of an examined patient from medical examination data read out at step S201. Recognition processing of patient information performs, for example, processing to extract information for identifying a patient, such as a patient ID (object identification information) from header information of medical images (DICOM headers in case of DICOM images) or electronic carte.

At step S203, the CPU 100 searches the medical document database 2 and the medical image database 3 using, as a term of search, the patient information recognized from the patient information recognition processing of step S202. Subsequently, processing to extract one or more past schemas and medical image data of an examined patient is performed. This will be called past examination record extraction processing. The extracted data is then stored in the magnetic disc 102. At this point, if data from a plurality of examination data are extracted, a new examination data number "i" is assigned to the schema and medical image data in the order of examination date.

Fundamentally, schema in which the disease locus is drawn is created every time when the physician performs diagnosis of an image. And, the created schema and medical image are respectively stored in the medical document database 2 and the medical image database 3. In other words, data which are diagnosed are those that have matching pairs (1 to 1) of schema and medical image and stored in respective databases. Further, information regarding a corresponding medical image is associated to and recorded in a schema.

Accordingly, in this processing, the schema and medical images of the patient of interest are extracted from the respective databases, and the pairs of schema and medical image of the same order (i.e., i-th schema and i-th medical image) are correlated using the information recorded in each schema as a key and stored in the magnetic disc 102.

However, cases in which either a schema or an image is missing are conceivable. In such cases, for example, examination data number is assigned to all data including those data which are not paired up, the missing part of unpaired data also having an examination data number as blank data. Alternatively, unpaired data can be skipped from the examination data number counting.

Further, in order to reduce work when drawing body parts, schema recorded in the medical document database 2 are those that are drawn on templates selected by the physician from the numerous basic schema templates pre-stored in the apparatus. Accordingly, each schema is separated into a "basic schema" and a "disease locus schema", and recorded in the medical document database 2.

At step S204, the CPU 100 stores numerical value 1 in the examination data number i which is to be processed. Also, the CPU 100 stores the extracted total number of past examination records of an examined patient as a constant n.

At step S205, the CPU 100 reads out, from the magnetic disc 102 and the main memory 101, the i-th examination data of the examined patient, i.e., the i-th schema and the i-th medical image.

At step S206, the CPU 100 performs, on the i-th schema read out to the main memory 101 at step S205, processing to extract structural information of body parts drawn in the schema and location and area information of the disease locus. As mentioned above, each schema is separated into a basic schema and a disease locus schema and stored.

FIG. 3 shows an example in which characteristic features (points) in a contour line of a body part (parts that are circled in the figure) are extracted as structural information of the body part drawn in the basic schema. Features in the contour line such as branching points, locations with dramatic increase in curvature, etc, are used as feature points in the extraction.

There are several variant methods which can be used as a method of extracting structural information of body part drawn in a basic schema. A method of inputting structural information of body part as attribute information into a basic schema at the time of creating the schema, is one method which can be employed. In that case, for example, it is possible to recognize the group a (particular) basic schema belongs to from a list of basic schema levels, location of the body part and name of the organ, as well as orientation of the body part (frontal view, left-side view, right-side view). Further, as methods of automatically extracting structural information of a body part, a method in which the CPU 100 calculates Scale-Invariant Feature Transform (SHIFT) feature amount suggested in non-patent reference 1, and a method in which the CPU 100 calculates Principal Component Analysis (PCA)-SHIFT feature amount suggested in non-patent reference 2 are available.

Further, as a method of extracting location and area information of the disease locus (disease locus information) drawn in a disease locus schema, following methods can be considered.

Figure 4:
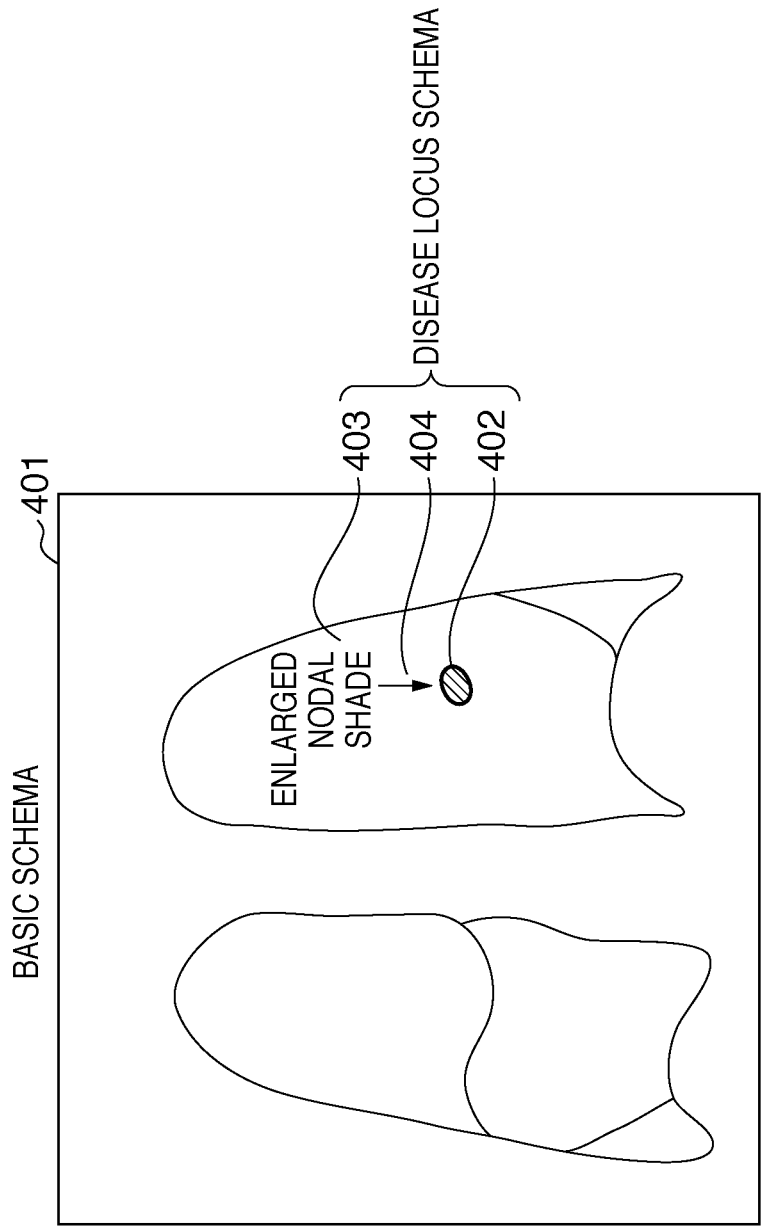
FIG. 4 shows a schema of a troubled part according to the first embodiment.

FIG. 4 shows a disease locus schema drawn on top of a basic schema 401 which indicates a body part having a disease locus. A disease locus schema is made from the following 3 types of information (parts):

Drawing 402 which expresses the mental picture of the physician regarding the condition of the disease locus (referred to as disease locus drawing)

Text 403 which explains disease locus drawing (referred to as disease locus explanation)

Arrow 404 pointing from disease locus explanation to disease locus drawing and connecting the two parts (referred to as connecting arrow)

In other words the location and area information of a disease locus can be extracted from the disease locus drawing 402. As shown in FIG. 4, although the disease locus explanation 403 and the connecting arrow 404 are made of line components, the disease locus drawing 402 is often expressed as an enclosed shape (figure) surrounded by a borderline in order to clearly indicate location and area of the disease locus. Accordingly, it is possible to retrieve the shape of the disease locus drawing by applying, for example, the variable shape model proposed in non-patent reference 3 which allows extraction of areas surrounded by edges. Subsequently, by calculating coordinates of the center portion of the diseased locus drawing, it is possible to roughly calculate the location (superior, intermediate or inferior lobes in case of the lung) of the disease locus.

As discussed in patent reference 2, when the three structural elements of a disease locus schema are stored separately as electronic data, the location and area of the disease locus drawing can be directly read out.

In step S207, the CPU 100 performs, on the ith medical image read out to the main memory 101 at step S205, processing to extract structural information of the body part shown in the medical image and candidate information of location and area of the disease locus. When extracting structural information of body part shown in a medical image, the extracted structural information must be information that can be compared to structural information of the body part drawn in the basic schema.

Similar to the method of extracting structural information of body parts drawn in a basic schema, there are several methods of extracting structural information of body parts shown in a medical image. For example, a method of displaying a medical image on the monitor 104 and having the physician indicate locations of characteristic features on the contour line of the body part shown in the medical image can be used. When employing this method, the characteristic features pointed out by the physician are to be selected to correspond to the feature points on the contour line of the basic schema shown in FIG. 3. Otherwise, methods of automatically calculating above mentioned SHIFT feature amount or PCA-SHIFT feature amount can also be used.

As a method of extracting candidate information of location and area of the disease locus shown in a medical image, a method utilizing Computer Aided Diagnosis (CAD) for extraction is known. As an example, lung cancer, which has a high rate of occurrence and a high risk of death, will be explained. Protopathic lung cancer appears as nodes which are close in shape to spheres. By applying a filter which intensifies the spherical shade, and applying a threshold processing on the intensified images, it is possible to automatically extract area of candidate shade indicating lung cancer, i.e., area of candidate shade indicating disease locus.

At step S208, the CPU 100 compares the body part and the structural information of the disease locus drawn in the i-h schema extracted in step S206, with the body part and the structural information of the disease locus shown in the i-h medical image extracted in step S207. Then, body part correlation is performed by calculating geometric correlation between the body part and the structural information of the disease locus drawn in the i-h schema and the body part and the structural information of the disease locus shown in the i-h medical image (referred to as structural information correlating processing). At this point, if the medical image is comprised of a 3-dimensional image or multiple 2-dimensional images, a cross-section image having the same orientation as that of the schema is identified within the image data, and the schema is correlated with the detected cross-section image.

Any of the coordinates of feature point, SHIFT feature amount and PCA-SHIFT feature amount, which are mentioned as structural information, can be thought of as vector information comprised of multiple components. Accordingly, the actual processing at step S206 is to search for vector information from the basic schema and the medical image which can form a pair. In this processing, the inter-vector distances between a single vector information of the basic schema and a single vector information of the medical image, and select the vector combination which yields the smallest distance among all vector combinations. However, when the inter-vector distance is larger than a predetermined threshold value, then it is decided that there is no matching vector pair. Furthermore, as a measure of reducing search misses of matching vectors, a number of vectors within proximity can be calculated instead of just one vector, which then can be treated as higher order vectors. In such case, inter-vector distance between the high dimension vector of the basic schema and the high dimension vector of the medical image is calculated.

The orientation of the body part drawn in the basic schema is extracted as part of the structural information of the body part in step S206. If the medical image is a 3-dimensional image, determination of the orientation of the body part leads to determination of orientation of image cross-sections, such as axial cross-section, coronal cross-section, and sagittal cross-section, is also determined. However, in 3-dimensional images, even when the orientation of image cross-section is determined, there can be plural cross-section images. Among these cross-section images, an image in which the disease locus is best shown is selected. In order to select an image, it is necessary to identify the actual disease locus from the 3-dimensional image. At this point, since areas of candidate shades of the disease locus have already been extracted in step S207, the actual disease locus is identified from the candidate shades.

As a method of disease locus identification, there is a method of utilizing information regarding disease locus which is obtained beforehand. In progress (or long term) observations, if there are images which are taken earlier than the i-th medical image that is to be processed, it is possible to estimate, to a certain extent, size, location and luminance distribution of the disease locus from the earlier image. If these types of information are stored as examination record before the time of examination of the i-th image, it is possible to narrow down the actual disease locus from all the candidate shades based on such stored information. Further, each of the cross-section images has the same orientation as the schema, and the location and area of the disease locus in the schema is already known to a certain extent from step S206. Thus, it is possible to identify the disease locus, by comparing the location and area of the candidate shades within each of the cross-section images with the approximate location and area of the disease locus in the schema, and detecting candidate shade(s) that match. Using this method, it is possible to correlate disease loci between the schema and the images. As a method of selecting a cross-section image with the best view of the disease locus, there is a method of selecting the cross-section image in which the area of the identified disease locus is largest.

At step S209, the CPU 100 increments the examination data number i (i.e., increase by 1).

At step S210, the CPU 100 moves either to step S205 if the value of the examination data number i is smaller than the total number "n" of past examination records, or otherwise moves to subsequent steps S211 and S212.

At step S211, using data of disease locus schema from schema 1 to n, the CPU 100 performs processing to generate a schema which allows understanding of temporal transitions of the disease loci in schema 1 to n (referred to as a disease locus time-series schema). Further, this processing is to be called "disease locus time-series schema generating processing".

At this point, the collection of disease locus schema are correlated, the above-mentioned 3 parts that comprise a disease locus are separated, and if the coordinates of parts are known, a time-series schema is generated by correcting the shape to one that is suited for display.

In regard to the disease locus drawing within the disease locus schema, since location of the disease locus fundamentally does not change, the disease locus drawing should be drawn at nearly-identical places on each of the schema that are created on differing dates. Accordingly, the coordinates for placing the disease locus drawing is used without any modification. However, disease locus explanation and connecting figures can be freely placed by the physician, making their placement inconsistent between disease locus schema. For this reason, if, for example, display of disease locus schema is alternated at the same location, disease locus explanations are displayed at different places, making them hard to see. To address this, the average values of the coordinates of disease locus explanations in disease locus schema numbered 1 to n, and the coordinates of the disease locus explanation in each of the disease locus schema is changed to the calculated average value. Subsequently, the connecting arrows can be structured such that they connect the disease locus drawings and the disease locus explanations, the coordinates of which have been shifted.

At step S212, for each medical images numbered 1 to n, the CPU 100 extracts ROI images that surround the disease locus as disease locus image information from cross-section images that are correlated to schema in step S208. Then, processing is performed to generate images that allow understanding of temporal transitions of these disease locus ROI images (referred to as time-series image data of disease locus). Further, this processing is to be referred to as time-series image data generating processing of disease locus.

As a method of determining extraction area of ROI images, a method described below is available. Since the area of disease locus has already been extracted at step S208, it is possible to obtain an image with the largest disease locus from the medical images numbered 1 to n. By calculating the area of the smallest rectangle or circle which encloses the largest disease locus added with a margin of fixed width, it is possible to determine the extraction area of a common ROI image for all medical images numbered 1 to n.

At step S213, the CPU 100 performs processing to run the time-series schema of disease locus generated at step S211 and the 2 time-series data of disease locus generated at step S212 in conjunction for display on the monitor 104. This processing will be referred to as simultaneous presentation processing of disease locus time-series data.

Figure 5:
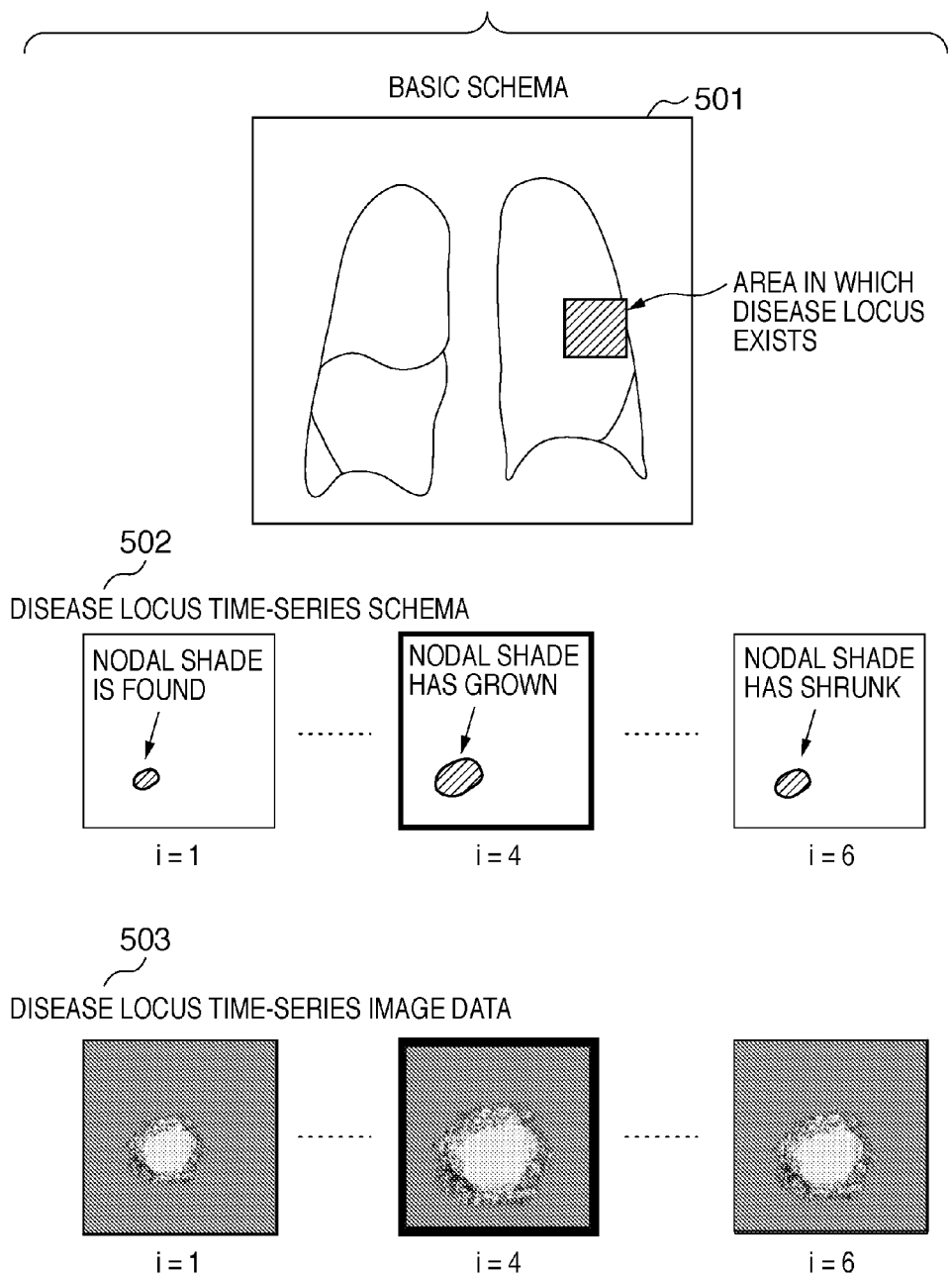
FIG. 5 shows simultaneous display of a time-series schema of a disease locus and their respective time-series images.

FIG. 5 shows an example of simultaneously running and displaying a pair of a disease locus time-series schema and a disease locus time-series image data. Numeral 501 in FIG. 5 indicates a basic schema in which a body part having a disease locus is drawn, on which the location of the disease locus is also displayed. Numeral 502 indicate a disease locus time-series schema, and numeral 503 indicates images within the corresponding disease locus time-series image data.

The disease locus time-series schema 502 simultaneously displays images, which are arranged in the order of increasing examination data number 1 ($1 \le i \le n$), i.e. in chronological order. Likewise, the disease locus time-series image data 503 displays images in the order of increasing examination data number i. By doing so, the operator of the diagnosis supporting apparatus 1 can observe temporal changes of the disease locus from both the disease schema and the disease locus images.

Further, the i-th disease locus schema and the i-th disease locus image are correlated. Taking advantage of this, when i-th data of one type is selected from the correlated 2 types of display information, it is possible to highlight data corresponding to the display information of the other type. For example, if the i-th schema from the disease locus time-series schema is selected, the correlated i-th disease locus image is highlighted. Further, selection and display in reverse order are also possible. As a method of highlighting, display frames of the i-th disease locus schema and image can be displayed in color. Alternatively, there are methods such as displaying other schema and images half-transparently. By doing so, the operator of the diagnosis supporting apparatus 1 can simultaneously understand the disease locus time-series schema and the disease locus time-series image data of the same examination data number.

Further, by selecting a plurality of data in one of the two types of display information (disease locus time-series schema and disease locus time-series image data), it is possible to highlight a plurality of data from the other type that correspond the selected plurality data. By doing so, it is possible to make comparison of two types of display information between a plurality of data having different examination data numbers at the same time. For example, if two schema having different examination numbers are selected from the disease-locus time-series schema, the corresponding disease-locus images are highlighted, making the comparison easy.

As explained above, with the diagnosis supporting apparatus 1 of the first embodiment, the operator of the diagnosis supporting apparatus 1, the operator of the diagnosis supporting apparatus 1 can observe temporal changes of the disease locus both in the disease locus schema and the disease locus images. By referring to the disease locus images together with the disease locus time-series schema, it is easy to understand the transitions in how the physician characterized and diagnosed the disease locus.

Additionally, by simultaneously referring to both the disease locus time-series schema and the disease locus time-series image data, it is possible to simultaneously view the information regarding the physician's diagnosis and the original images of the disease locus while observing temporal changes of them. From this, it is possible to use both subjective evaluation and raw information of the past as reference, allowing provision of information which is helpful in diagnoses in long term observations.

VARIANT EXAMPLE 1

The simultaneous display of the disease locus time-series schema and the disease locus time-series image data at step S213 can also follow the method provided below.

Figure 6:
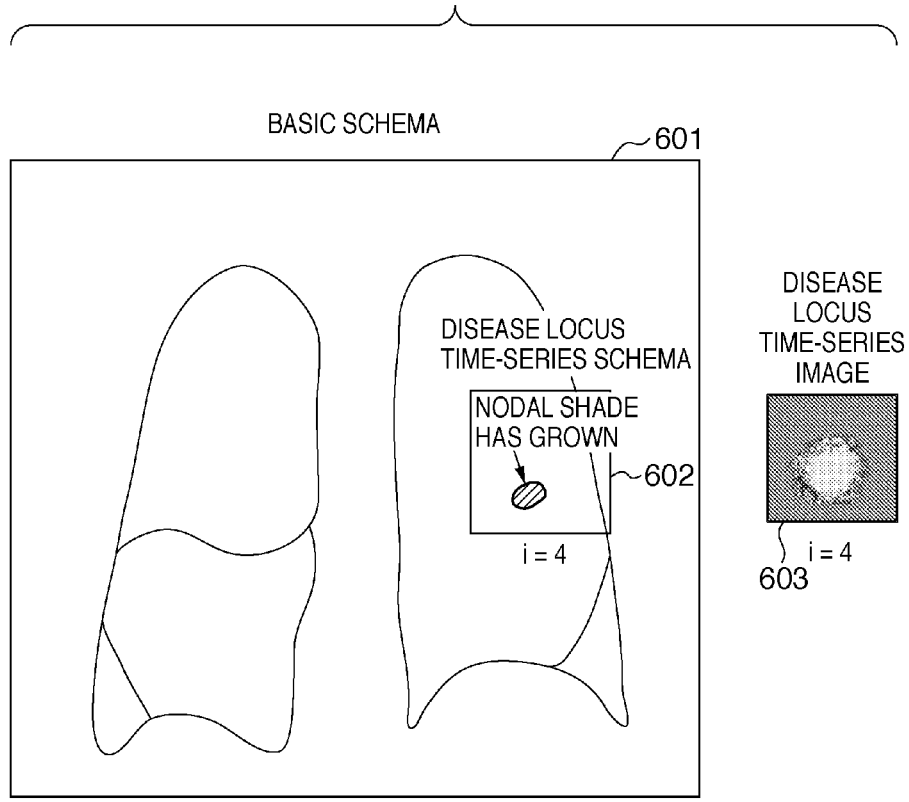
FIG. 6 shows a different example of simultaneous display of a time-series schema and a time-series image of a disease locus.

FIG. 6 shows an example in which the basic schema is overlapped with the disease locus time-series schema. Numeral 601 indicates a basic schema on which a body part having a disease locus is drawn, and a disease locus time-series schema 602 is also shown on top of this basic schema. Numeral 603 indicates an image within the disease locus time-series image data which correspond to the disease locus time-series schema. In the disease locus time-series schema 602, the disease locus schema of the selected examination data number i is displayed on a particular display area (on the basic schema), and every time the value of i is refreshed, a corresponding diseased locus schema is displayed on the display area. Similarly, the disease locus time-series image data 603 also displays the disease locus schema of the selected examination data number i, and every time the value of i is refreshed, a corresponding diseased locus schema is displayed on the display area.

Similar to FIG. 5, the two types of display information are correlated by the examination data number i, and when the examination data number i is selected, the 2 types of i-th display information are simultaneously displayed in sequence. As a method of selecting the data of the examination data number i, a method which continuously adds the value of i automatically in a program, or a method which refreshes the value of i in response to a mouse click or drag, are available. By doing so, the images within the disease locus time-series schema and the disease locus time-series image data can be displayed as moving images (animation display) on the display area.

By having such structure, it is possible to get a direct understanding of continuous changes. Further, by switching the display of the disease locus time-series schema on top of the basic schema, it is possible to seamlessly grasp information regarding both the body part and the disease locus.

(Second Embodiment)

In the second embodiment, a configuration in which a schema and the feature amount of the disease locus image corresponding to the schema are displayed in conjunction will be explained. The structure of the diagnosis supporting apparatus according to the second embodiment will be omitted since it is identical to that according to the first embodiment. However, as explained below, the control program executed by the CPU is different from that of the first embodiment. In other words, the program stored in the magnetic disc 102 is different.

Figure 7:
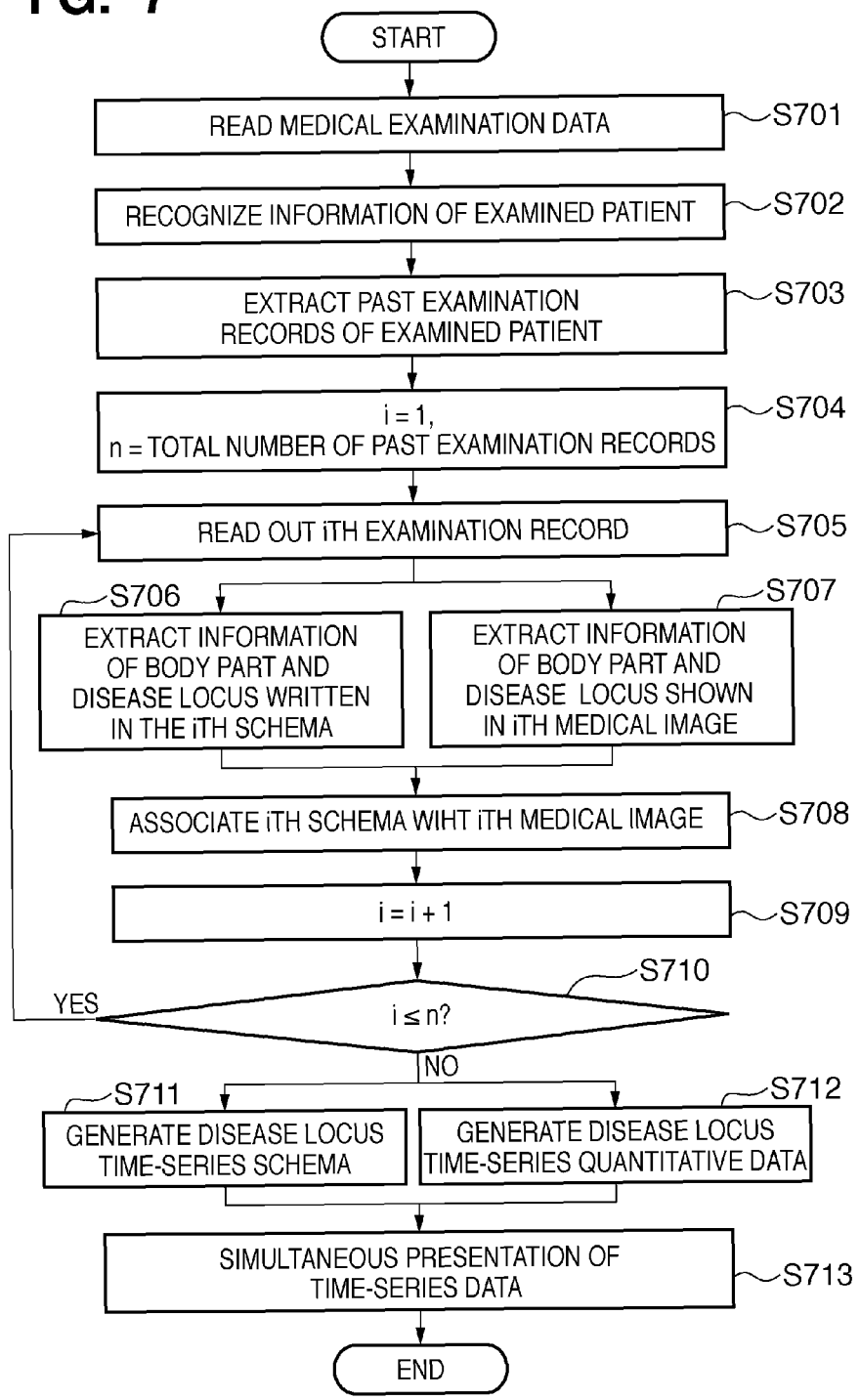
FIG. 7 is a processing flow chart of the diagnosis supporting apparatus 1 according to a second embodiment.

FIG. 7 is a flowchart of operation of the diagnosis supporting apparatus according to the second embodiment. Detailed explanation of steps in which processing that are identical to those shown in the flow chart in FIG. 2 of the first embodiment will be omitted.

Processing in steps S701 to S711 are identical to those in steps S201 to S211 of the first embodiment.

At step S712, the CPU 100 calculates, for the $1^{st}$ to the nth medical images, quantitative data of the disease locus area within images that are correlated with the disease locus of a schema. Then, using the quantification data, processing is performed which generates data that allows quantitative understanding of the disease locus area. This processing will be called disease locus time-series image feature amount generation means.

At this point, quantitative information which is useful for diagnosis is extracted from the disease locus area data that is extracted at step S707. For example, if a shade of a node is found and is suspected to be lung cancer tissue in a thoracic CT image, one type of information which could be helpful in diagnosis of such image is the size of the node. Accordingly, in this case, an effective radius R of the disease locus area is calculated. The effective radius R is, for example, assigned using equation (1) or (1') shown below:

$$R=\text{(the radius of a circle having which is equal in area to that of the disease locus derived based on image)} \quad (1)$$

$$R=\text{(the radius of a sphere which is equal in volume to that of the disease locus derived based on image)} \quad (1')$$

Figure 8:
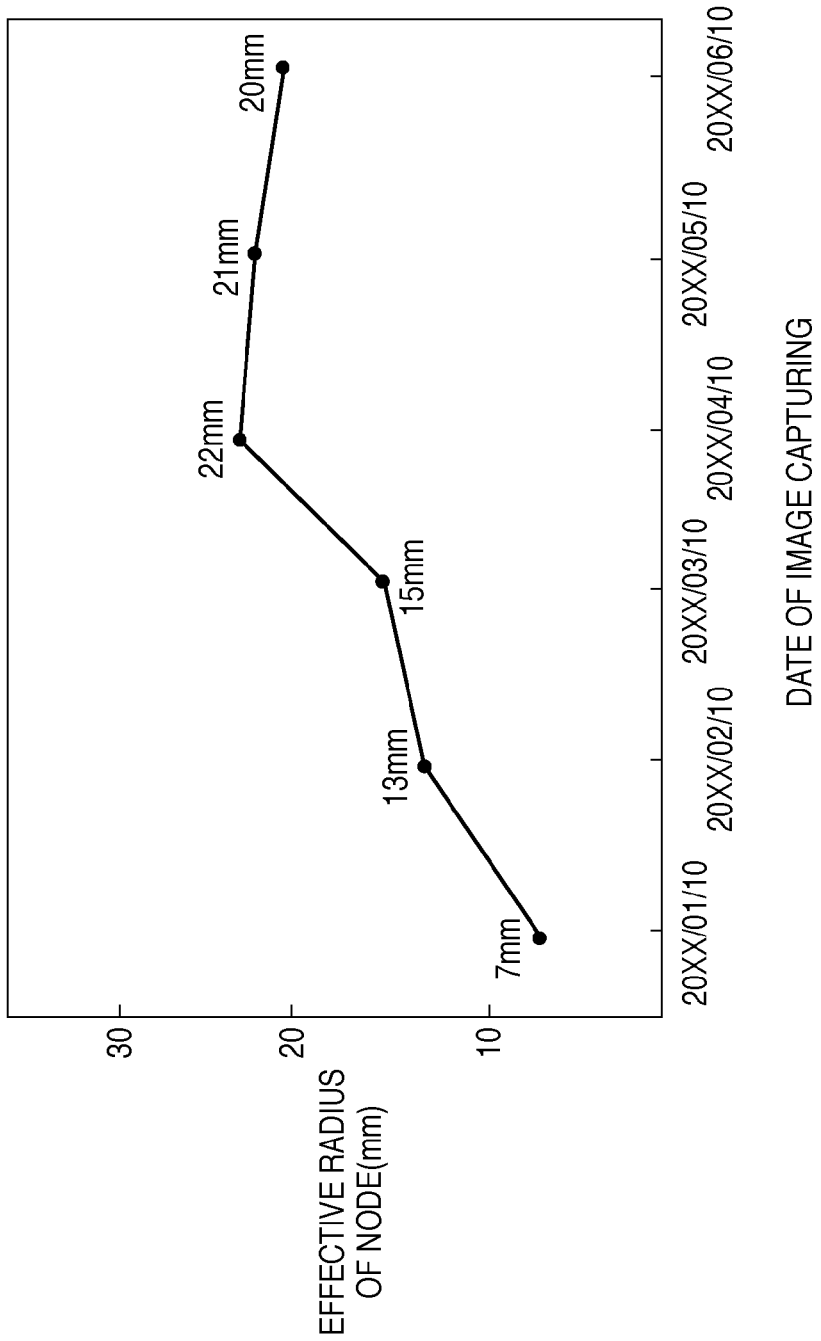
FIG. 8 shows a graph of temporal changes of a disease locus according to the second embodiment.

By calculating an effective radius for each of the medical images taken on different dates using equation (1), it is possible to generate disease locus time-series quantitative data. As disease locus time-series quantitative data, it is possible to create, for example, a graph showing quantitative changes in node size as shown in FIG. 8 (referred to as disease locus temporal change graph). FIG. 8 shows a graph with plotted points, in which the horizontal axis is the time of capturing medical image and the vertical axis is the value of effective radius R.

At step S713, the CPU 100 performs processing to display the disease locus time-series schema generated at step S711 in conjunction with the disease locus time-series quantitative data generated at step S712. This processing will be referred to as simultaneous presentation processing of disease locus time-series data, as it was called in step S213 of the first embodiment.

Figure 9:
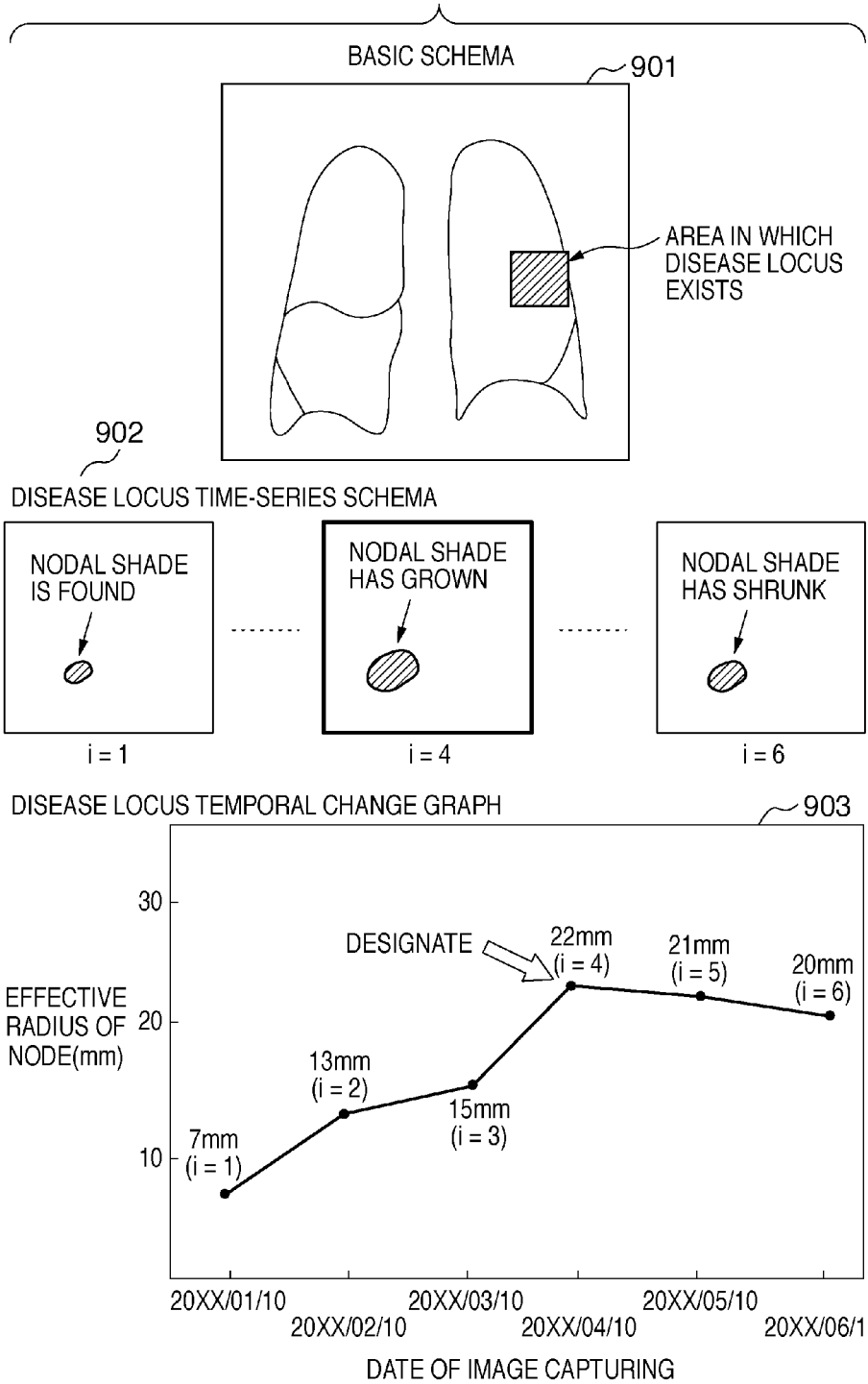
FIG. 9 shows simultaneous display of a time-series schema and a graph of temporal changes of the disease locus.

FIG. 9 shows an example of displaying a disease locus time-series schema in conjunction with a disease locus temporal change graph which is generated as an example of disease locus time-series quantitative data.

901 indicates a basic schema of a body part to which the disease locus belongs, which also displays the location of the disease locus. 902 is a disease locus time-series schema, and 903 is a corresponding disease locus time-series graph. In FIG. 9, size of node is utilized as a quantitative value of disease locus. Like the simultaneous presentation shown in FIG. 9, it is possible to display the disease locus time-series schema 902 in conjunction with the disease locus time-series graph 903. For example, if the i-th point in the disease locus temporal change graph 903 is selected, it is possible to highlight the correlated i-th disease locus schema. As methods of highlighting, displaying the i-th disease locus schema with a colored frame, displaying the disease locus schema other than the one selected half-transparently, etc., are known.

Further, for example, by moving the designated point along the time-series on the disease locus temporal change graph 903, it is possible to synchronize the changes in the above-mentioned 2 types of information and highlight them for display. As a method of moving designated point on the graph, for example, the points on the line can be clicked in sequence with a mouse, or the designated point can be dragged from one point to another. Alternatively, a method which uses a control bar corresponding to the horizontal axis of the graph for changing the designated point can be used. It is also possible to arrange such that when two points having differing examination data numbers are selected from the graph, the corresponding two disease locus schema are highlighted.

As explained above, according to the second embodiment, the operator of the diagnosis supporting apparatus 1 can observe temporal changes of the disease locus from both the disease locus schema and quantitative data derived from the disease locus images.

VARIANT EXAMPLE 1

Generation the disease locus time-series quantitative data at step S712 and the coupled presentation of the time-series data at step S713 can also be arranged as follows.

FIG. 10 shows a disease locus temporal change table which shows the quantitative data of the disease locus organized into a table. Like the disease locus temporal change graph of step S712, effective radii of nodal shades are shown as quantitative data of the disease locus.

Then in step S713, processing to display the disease locus time-series schema and the disease locus temporal change chart in conjunction is performed. For example, when a specific examination data is selected in the disease locus temporal change chart, the data in the corresponding disease locus time-series schema can be highlighted for display.

VARIANT EXAMPLE 2

Generation of the disease locus time-series quantitative data at step S712 can be configured as follows.

As quantitative data of the disease locus, the effective radius of the nodal shade extracted from the image data was used at step S712. However, applicable quantitative data of the disease locus is not limited to this. For example, in situations where soft tissues such as tumor in the interior of lymph nodes are included and where liquefied tissues due to necrosis of these tissues are included, the average density value and dispersion of these areas differ. Generally, soft tissues tend to have higher density values than the liquefied tissues, and because liquefied tissues have uniform density values they also tend to have smaller dispersion. As such, it can also be suitable to generate, as quantitative data which characterizes the condition of the disease locus, disease locus time-series quantitative data by applying average of image density values and dispersion values of the interior of the disease locus area in image data.

(Third Embodiment)

In the third embodiment, an example will be explained in which two or more types of data are displayed in conjunction with a schema. In other words, in the first and second embodiments, as information which is to be displayed in conjunction with the disease locus time-series schema, disease locus time-series images and disease locus time-series quantitative data were respectively used. However, the information to be displayed in conjunction with the disease locus time-series schema is not limited to only 1 type of information.

For example, it is also possible to present 3 types of information, the disease locus time-series schema, the disease locus time-series images and the disease locus time-series quantitative data, in conjunction. Also, when using disease locus temporal change graph as the disease locus time-series quantitative data, the following method of displaying in conjunction is available. It can be configured to display as moving images (animation display) corresponding disease locus time-series schema and disease locus time-series image by designating points on the graph in order using a device such as a mouse.

As explained above, according to the third embodiment, the operator of the diagnosis supporting apparatus 1 can check a plurality of data at each of the time points corresponding to each of schema.

(Fourth Embodiment)

In a fourth embodiment, an example using similar case data as information which is displayed in conjunction with a schema will be explained. In other words, although previous embodiments used data that can be obtained from past examination images only as the information presented with the disease locus time-series schema, the information that can be presented with the disease locus time-series schema are not limited to examination data of the object him/herself.

For example, there is a method of simultaneously displaying examination images of an object with past examination images of other patients whose images resemble those of the object (referred to as similar images). As an acquisition method of similar images, for example, there is a method of acquiring examination images of a patient by searching the database for patients' carte having matching diagnosis information, using, as a keyword, information of confirmed diagnosis provided in the carte pertaining to the patient being examined and retrieving examination images from them. Alternatively, a method in which an image feature amount is extracted from an image of a disease locus from the examined patient, and an image is acquired which has the closest feature amount from a database that stores past examination images of various types in large quantities, can also be used.

After acquiring a similar image, it is possible to generate a time series of similar images (referred to as similar case time-series image data) when there are other examination images of the same patient. The processing up to this point will be referred to as similar case time-series image data generation processing. As a method of displaying a time series of similar images, they can be presented in conjunction with the disease locus time-series images, with the state of disease progression (e.g. radius of a detected node) as a reference. As a method the plurality of schemas and on image feature amounts of disease locus areas of medical image data related to each of the plurality of schemas; and synchronizing and displaying the plurality of sc detected node in which is suspected of lung cancer.

As explained above, according to the fourth embodiment, the operator of the diagnosis supporting apparatus 1 can make observations while making comparison between disease locus schema or corresponding disease locus image with disease locus images of similar cases.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-246596, filed Sep. 25, 2008, which is hereby incorporated by reference herein in their entirety.

What is claimed is:

1. An information processing apparatus for supporting a diagnosis comprising:
a first unit configured to acquire area information indicating an area of a disease locus, to which an explanation text is added, recorded on a schema for an object; and
a second unit configured to extract, based on the acquired area information, a region corresponding to the disease locus from a medical image data for the object.

2. The information processing apparatus according to claim 1, further comprising a third unit configured to control so that a display unit displays the extracted region.

3. The information processing apparatus according to claim 2, wherein the schema comprises a plurality of schemas, which are recorded at a different point in time, and the third unit controls so that the plurality of schemas and the extracted region are displayed in a form that both the plurality of schemas and the extracted region are related chronologically.

4. The information processing apparatus according to claim 1, wherein the second unit limits, based on the acquired area information, a location and area of a candidate shade obtained from the medical image data for the object.

5. A non-transitory computer-readable recording medium storing a program that causes a computer to function as each of the units of the information processing apparatus according to claim 1.

6. An information processing apparatus comprising:
an acquiring unit configured to acquire a plurality of schemas, which are recorded at a different point in time, related to an object and medical image data corresponding to disease locus information, which includes an explanation text, recorded in each of the plurality of schemas;
a deriving unit configured to derive an image feature amount of a disease locus area for each of the medical image data respectively related to each of the plurality of schemas;
a time-series image feature amount generating unit configured to generate time-series image feature amounts of the disease locus area based on time information of each of the plurality of schemas and on image feature amounts of disease locus areas of medical image data related to each of the plurality of schemas; and
a display control unit configured to synchronize and display the plurality of schemas and the time-series image feature amounts of the disease locus on a display unit.

7. The information processing apparatus according to claim 6, wherein the image feature amount is size of the disease locus area.

8. The information processing apparatus according to claim 6, wherein the image feature amount is image density value of the disease locus area.

9. An information processing method for supporting a diagnosis comprising the steps of:
acquiring area information indicating an area of a disease locus recorded on a schema for an object; and
extracting, based on the acquired area information, a region corresponding to the disease locus, to which an explanation text is added, from a medical image data for the object.

10. An information processing method comprising the steps of:
acquiring a plurality of schemas, which are recorded at a different point in time, related to an object and medical image data corresponding to disease locus information, which includes an explanation text, recorded in each of the plurality of schemas;
deriving an image feature amount of a disease locus area for each of the medical image data respectively related to each of the plurality of schemas;
generating time-series image feature amounts of the disease locus area based on time information of each of the plurality of schemas and on image feature amounts of disease locus areas of medical image data related to each of the plurality of schemas; and
synchronizing and displaying the plurality of schemas and the time-series image feature amounts of the disease locus on a display unit.

11. An information processing apparatus for supporting a diagnosis comprising:
a first unit configured to acquire area information indicating an area of a disease locus, to which an explanation text is added, recorded on a schema for an object; and
a second unit configured to extract, based on the acquired area information, a region corresponding to the disease locus from a medical image data for the object,
wherein said second unit identifies, if the medical image comprises a three-dimensional image or multiple two-dimensional images, a cross-section having the same orientation as that of the schema and extracts a region corresponding to the disease locus.

12. An information processing apparatus comprising:
an acquiring unit configured to acquire a plurality of schemas, which are recorded at a different point in time, related to an object and medical image data corresponding to disease locus information, which includes an explanation text, recorded in each of the plurality of schemas;
a deriving unit configured to derive an image feature amount of a disease locus area for each of the medical image data respectively related to each of the plurality of schemas;

a time-series image feature amount generating unit configured to generate time-series image feature amounts of the disease locus area based on time information of each of the plurality of schemas and on image feature amounts of disease locus areas of medical image data related to each of the plurality of schemas; and a display control unit configured to synchronize and display the plurality of schemas and the time-series image feature amounts of the disease locus on a display unit, wherein said deriving unit identifies, if the medical image comprises a three-dimensional image or multiple two-dimensional images, a cross-section having the same orientation as that of the schema and extracts a region corresponding to the disease locus.

13. An information processing method for supporting a diagnosis comprising the steps of:

acquiring area information indicating an area of a disease locus recorded on a schema for an object; and extracting, based on the acquired area information, a region corresponding to the disease locus, to which an explanation text is added, from a medical image data for the object, wherein said extracting step includes identifying, if the medical image comprises a three-dimensional image or multiple two-dimensional images, a cross-section having the same orientation as that of the schema and extracting a region corresponding to the disease locus.

14. An information processing method comprising the steps of:

acquiring a plurality of schemas, which are recorded at a different point in time, related to an object and medical image data corresponding to disease locus information, which includes an explanation text, recorded in each of the plurality of schemas;

deriving an image feature amount of a disease locus area for each of the medical image data respectively related to each of the plurality of schemas;

generating time-series image feature amounts of the disease locus area based on time information of each of the plurality of schemas and on image feature amounts of disease locus areas of medical image data related to each of the plurality of schemas; and synchronizing and displaying the plurality of schemas and the time-series image feature amounts of the disease locus on a display unit, wherein said deriving includes identifying, if the medical image comprise a three-dimensional image or multiple two-dimensional images, a cross-section having the same orientation as that of the schema and extracting a region corresponding to the disease locus.

* * * * *